United States Patent
Klimchak et al.

[11] Patent Number: 6,120,795
[45] Date of Patent: Sep. 19, 2000

[54] MANUFACTURE OF LIPOSOMES AND LIPID-PROTEIN COMPLEXES BY ETHANOLIC INJECTION AND THIN FILM EVAPORATION

[75] Inventors: Robert Joseph Klimchak, Flemington, N.J.; Peter G. Glavinos, Jr., deceased, late of Dayton, Ohio, by Peter G. Glavinos, Sr., administrator

[73] Assignee: Ortho Pharmaceutical Corp., Raritan, N.J.

[21] Appl. No.: 08/810,576

[22] Filed: Mar. 4, 1997

Related U.S. Application Data

[60] Provisional application No. 60/014,227, Mar. 27, 1996.

[51] Int. Cl.[7] .................. C07K 14/785; A61K 35/16; A61K 9/121; A61K 9/00
[52] U.S. Cl. ................. 424/450; 424/1.21; 514/2; 514/12
[58] Field of Search ................. 514/2, 13; 424/450

[56] References Cited

U.S. PATENT DOCUMENTS

| | | | |
|---|---|---|---|
| 4,515,736 | 5/1985 | Deamer | 264/4.3 |
| 4,902,466 | 2/1990 | Law | 264/299 |
| 4,935,171 | 6/1990 | Bracken | 264/4.6 |
| 5,028,297 | 7/1991 | Bracken | 159/6.3 |
| 5,260,273 | 11/1993 | Cochrane et al. | 514/12 |
| 5,262,168 | 11/1993 | Lenk | 424/450 |
| 5,277,914 | 1/1994 | Szoka, Jr. | 424/450 |
| 5,567,434 | 10/1996 | Szoka | 424/250 |

FOREIGN PATENT DOCUMENTS

| | | |
|---|---|---|
| WO 91 16039 | 10/1991 | European Pat. Off. . |
| 40 38 075 | 3/1992 | European Pat. Off. . |
| WO 92/06703 | 4/1992 | European Pat. Off. . |
| WO 97 19108 | 5/1997 | European Pat. Off. . |

OTHER PUBLICATIONS

Szoka et al. Ann. Rev. Biophys. Bioeng. 9:467–508, Jan. 1980.

Biochimica Et Biophysica Acta, 298(1973) pp. 1015–1019 Elsevier Scientific Publishing Company, Amsterdam. Single Bilayer Liposomes Prepared Without Sonication.

*Primary Examiner*—Michael P. Woodward
*Assistant Examiner*—Michael Borin
*Attorney, Agent, or Firm*—Kenneth J. Dow

[57] ABSTRACT

A method for preparing liposomal suspensions which comprises preparing a solution of a poorly soluble protein or other poorly soluble compound and an encapsulating amount of a suitable lipid in an alcoholic solvent, injecting the resulting solution into an aqueous solution of appropriate ionic strength, and removing the alcoholic solvent by thin-film evaporation at the transition temperature of the liposomal suspension. This process is suitable for continuous production on an industrial manufacturing scale. It is of particular application in the preparation of KL4 pulmonary surfactant composition, wherein the thin film evaporation is conducted within the transition temperature range of the surfactant (approximately 35–50° C.), thereby enhancing the KL4 peptide insertion into the lipid bilayer and leading to a product with reduced viscosity and enhanced surface tension lowering properties.

8 Claims, No Drawings

MANUFACTURE OF LIPOSOMES AND LIPID-PROTEIN COMPLEXES BY ETHANOLIC INJECTION AND THIN FILM EVAPORATION

This application claims benefit of Provisional Appl. 60/014,227 filed Mar. 27, 1996.

FIELD OF THE INVENTION

The present invention relates to the field of pharmaceutical compositions and the manufacture of liposomes and lipid-protein complexes by ethanolic injection. In another aspect, the invention relates to manufacture of synthetic lipid-protein pulmonary surfactant liposomal compositions suitable for the treatment of respiratory distress syndrome.

BACKGROUND OF THE INVENTION

Liposomes are small vesicles comprising amphipathic lipids arranged in spherical bilayers. Liposomes may contain many concentric lipid bilayers separated by aqueous channels (multilamellar vesicles or MLVs), or alternatively, they may contain a single membrane bilayer (unilamellar vesicles), which may be small unilamellar vesicles (SUVs) or large unilamellar vesicles (LUVs). The lipid bilayer is composed of two lipid monolayers having a hydrophobic "tail" region and a hydrophilic "head" region. In the membrane bilayer, the hydrophobic "tails" of the lipid monolayers orient towards the center of the bilayer, whereas the hydrophilic "heads" orient toward the aqueous phase.

Liposomes may be used to encapsulate a variety of materials by trapping hydrophilic compounds in the aqueous interior or between bilayers, or by trapping hydrophobic compounds within the bilayer. As such, they are particularly useful to deliver biologically active materials by encapsulating compounds which exhibit poor aqueous solubility or which exhibit unacceptable toxicity at therapeutic dosages.

Liposomes and related phospholipid vesicle complexes can be prepared by a variety of techniques. In general, these techniques start with "dry" lipids that are introduced into an aqueous phase (D. Lasic, J.Theor. Biol. (1087) 124:35–41). Once the lipid is hydrated, liposomes form spontaneously. Techniques have been developed to control the number of lamellae in the liposome and to produce defined particle size. U.S. Pat. No. 4,935,171 discloses a single-vessel method of preparing liposomes by forming a homogeneous lipid-film in a thin-film evaporator by evaporation of the organic solvent, followed by in-situ hydration of the film in an aqueous phase by agitation.

Another method of preparing liposomes is known as the ethanolic injection process. (S. Batzre et al., *Biochem. Biophys Acta* (1973) 298:1015–1019; J. Kremer at al., *Biochemistry* (1977) 16:3932–3935). In this process, the lipids are dissolved in ethanol and injected into the aqueous phase, optionally containing a buffer solution. This process generates unilamellar or multilamellar vesicles of defined size. One advantage of this process is that it permits continuous production of vesicles if the solvent can be removed in a continuous process. Generally, the procedure requires removal of the solvent following injection of the solvent into the aqueous phase. This is generally accomplished by dialysis or other filtration processes such as tangential flow filtration.

Pulmonary surfactant is a complex mixture of lipids and proteins that promotes the formation of a monolayer at the alveolar air-water interface and, by reducing the surface tension, prevents the collapse of the alveolus during expiration. Premature infants, and occasionally full term neonates, sometimes suffer from a condition known as respiratory distress syndrome (RDS) due to the lack of sufficient endogenous pulmonary surfactant. Artificial pulmonary surfactants have therefore been developed to treat this condition thereby reducing infant morbidity and mortality.

One of these artificial pulmonary surfactants, known as KL4, is disclosed in U.S. Pat. Nos. 5,164,369 and 5,260,273, hereby incorporated by reference into the present application. Disclosed therein is a synthetic pulmonary surfactant composition comprising a pharmaceutically acceptable phospholipid admixed with a polypeptide having alternating hydrophobic and positively charged amino acid residues. As formulated for clinical use, the composition is a liposome comprised of dipalmitoyl-phosphatidylcholine (DPPC), palmitoyloleoylphosphatidylglycerol (POPG), palmitic acid (PA) and the synthetic peptide KL4 suspended in a buffered aqueous medium. The final drug product is a viscous suspension intended for direct instillation into the lung.

At present, this liposomal KL4 composition is formulated by the aforementioned ethanolic injection process. As described above, it is general practice to remove the ethanol solvent from the composition by dialysis. However, the dialysis procedure is not satisfactory for the liposomal KL4 drug product due to the viscous nature of the product. There is thus a need for a method of removing the ethanol from liposomal formulations prepared by ethanolic injection where the liposomal formulation is viscous as in the case of KL4. Advantageously, the solvent removal process should allow for continuous removal of the solvent during the manufacturing process.

In addition, it is noted that the extent of KL4 peptide insertion and the subsequent manner with which it associates with the components of the liposome lipid bilayer must be optimal for drug product performance with respect to both surface tension lowering properties and viscosity (fluidity). One of the problems encountered in the formulation and performance of liposomal KL4 drug product is that the viscosity of the drug product can limit effective distribution in the lung, thereby reducing in vivo activity. The present invention is intended to improve performance of KL4 liposomal pulmonary surfactant by facilitating protein insertion into the lipid bilayer and reducing viscosity of the final drug product.

SUMMARY OF THE INVENTION

A method for preparing liposomal suspensions which comprises preparing a solution of a poorly soluble protein or other poorly soluble compound and an encapsulating amount of a suitable lipid in an alcoholic solvent, injecting the resulting solution into an aqueous solution of appropriate ionic strength, and removing the alcoholic solvent by thin-film evaporation within the transition temperature range of the liposomal suspension. This process is suitable for continuous production on an industrial manufacturing scale.

In accordance with the present invention, protein insertion into the lipid bilayer of the liposome is optimized by conducting the solvent removal by thin-film evaporation within the transition temperature range of the protein. Protein insertion into lipid bilayers is optimal under those conditions in which the bilayer exists in a state of flux between "gel" and "liquid crystalline" phases—the transition temperature phase. The alcoholic solvent increases the fluidity of the lipid bilayer, thus allowing protein diffusion to the bulk phase (water) surrounding the bilayer. By conducting thin-film evaporation within the transition temperature range of the surfactant, protein in the bulk phase inserts into the lipid bilayer with less effort as the bilayer remains fluid within the transition temperature range. Otherwise, protein may remain in the bulk phase outside the bilayer resulting in greater drug product viscosity, and reduced activity.

In the case of KL4 pulmonary surfactant composition, the thin film evaporation is conducted within the transition temperature range of the surfactant (approximately 35–50° C.), thereby enhancing the KL4 peptide insertion into the lipid bilayer and leading to a product with reduced viscosity and enhanced surface tension lowering properties.

DETAILED DESCRIPTION

The process of the present invention is carried out by dissolving the poorly soluble protein or other poorly soluble compound in an alcoholic solvent and adding an encapsulating amount of a suitable lipid(s). The resulting solution is then injected into an aqueous solution of appropriate ionic strength, forming the liposomes. The alcoholic solvent is then removed by thin-film evaporation conducted within the transition temperature range of the liposomal suspension.

The process is useful for the formulation into liposomes of poorly soluble proteins or other poorly soluble compounds for which liposomal delivery is desirable. Poorly soluble compounds are those which exhibit poor solubility (less than about 1 mg/ml) at physiologic temperature and pH in aqueous solution. As mentioned, the process is particularly suitable for formulation of KL4 pulmonary surfactant, but is applicable to formulation of other liposomal drug products such as doxorubicin, amphotericin B and the like.

The alcoholic solvent is a lower alkanol of one to six carbon atoms, such as methanol, ethanol, n-propanol, isopropanol, n-butanol and the like. Solubilizing amounts of fluorinated alcohols such as 2,2,2-triflouroethanol; 1,1,1,3,3,3-hexafluoro-2 propanol and the like may also be used as the solvent or may be added to the solvent mixture. The solvent may also optionally contain a solubilizing amount of an aprotic solvent such as dimethylsulfoxide (DMSO), dioxane, dimethylformamide (DMF) and the like.

The lipid is any of the known amphipathic lipid or phospholipid compositions generally used in the preparation of liposomes. Suitable lipids include dipalmitoyl-phosphatidylcholine (DPPC), palmitoyloleoylphosphatidylglycerol (POPG), palmitic acid (PA), egg phosphatidylcholine (EPC), egg phosphatidylglycerol (EPG), cholesterol, dimyristoylphosphatidylglycerol (DMPG), dimyristoylphosphatidylcholine (DMPC) and the like. The lipids are generally used in an amount sufficient to encapsulate the protein or poorly soluble compound and form liposomes of appropriate size. Selection of an appropriate encapsulating amount of the lipid will depend on the particular compound and process conditions selected and is within the skill of the art. (See G. Gregoriadis, "Liposome Technology" I-III CRC Press, Inc. Boca Raton Fla. 1984).

In accordance with known ethanolic injection procedures, the ethanolic/lipid suspension is injected into the aqueous solution by means of a syringe, perforated plate or tube or other appropriate extrusion means. Preferably, the aqueous solution may contain small amounts of buffering compounds, preservatives and the like. In the case of KL4 pulmonary surfactant, the solution of lipids and KL4 in ethanol is sterile filtered into sterile tris buffer at 45° C. with vigorous mixing.

Once the ethanolic injection procedure is completed, the ethanolic solvent is removed in accordance with the invention through the use of a thin-film evaporator. Thin-film evaporators are well known devices designed for continuous feed concentration of solutions. The device generally comprises an inner cylindrical evaporating chamber encircled by a thermal exchange jacket for providing proper temperature within the evaporating chamber. A rotatable shaft having rotor blades secured thereto is positioned within the evaporating chamber. The rotor blades extend radially from the rotor shaft and are spaced in a manner sufficient to establish a film-forming relationship with the inner wall of the chamber. In operation, the dilute solution is introduced into the evaporator chamber and a thin film of the solution is formed on the inner heat exchange surface of the chamber by the rotor blades. As the thin film is formed, heat or vacuum pressure applied to the chamber evaporates the solvent and concentrates the solution. The evaporation can be performed on a continuous basis by continuous introduction and extraction of the solution from the chamber.

A variety of thin-film evaporators are known in the art and are applicable for use in the present invention. For example, U.S Pat. Nos. 5,256,250 and 4,707,220 describe thin-film evaporators applicable for use in the process of the invention.

Thus, in accordance with the invention, a thin-film evaporator as described hereinbefore is used for the solvent removal following the ethanol injection process. Typically, in the case of KL4 pulmonary surfactant, the liposome suspension prepared by ethanol injection contains an amount of ethanol in the range of 5–20% w/w that is subject to removal by the thin-film evaporation process. Preferably, the solution fed into the thin film evaporator should contain no more than 25% w/w ethanol. Once the lipid/ethanol solution has been injected into the aqueous buffer, and the liposomal suspension is formed, the suspension is fed into the evaporation chamber of the thin-film evaporator through an inlet fitting designed for such purpose. The liposome suspension is introduced into the apparatus while the rotor is operating. A peristaltic pump can be employed to regulate the loading of the suspension into the chamber. Once the suspension is drawn into the chamber, the rotors act to distribute the suspension as a film on the interior of the heat-exchange walls, which are maintained within a temperature sufficient to keep the product at the appropriate transition temperature range. A vacuum is drawn on the chamber and the alcoholic solvent in the suspension is evaporated and drawn from the chamber through an outlet. The concentrated suspension then exits the chamber at the opposite end. The whole process can be performed on a continuous basis with the suspension being fed and extracted from the thin-film evaporator as appropriate.

During the evaporation process, the temperature of the heat exchange surface is maintained by the recirculating heating fluid in the thermal exchange jacket so that the internal temperature of the material in the evaporator is within the transition temperature range ($T_c$) of the surfactant. This is the temperature at which the lipid surfactant is in a state of flux between "gel" and "liquid crystalline" phases. In the case of KL4 pulmonary surfactant composition, the thin film evaporation is conducted within the transition temperature range of the DPPC:POPG:PA:KL4 surfactant (approximately 35–50° C.), thereby enhancing the KL4 peptide insertion into the lipid bilayer and leading to a product with reduced viscosity and enhanced surface tension lowering properties. During the liposome formation process, the ethanol solvent increases the fluidity of the lipid bilayer, thus allowing protein insertion into the lipid bilayer. By conducting thin-film evaporation within the transition temperature range of the surfactant composition, the peptide in the bulk phase inserts into the lipid bilayer more efficiently as the fluidity of the bilayer decreases due to solvent removal. Otherwise, KL4 peptide may remain in the bulk aqueous phase outside the bilayer resulting in greater drug product viscosity and reduced surface tension lowering properties. If the process is conducted below the transition temperature range, drug product viscosity is increased due to KL4 peptide that is either excluded from the bilayer (trapped outside during ethanol removal) or improperly incorporated into the bilayer. Surface tension lowering properties are compromised due to incomplete and incorrect KL4 bilayer insertion. Accordingly, the process of the present invention allows for manufacture of KL4 pulmonary surfactant with enhanced surface tension lowering properties and lower viscosity, both of which lead to optimal in vivo performance.

For liposomal compositions intended for pharmaceutical uses, the process of the invention may be carried out under aseptic conditions. This is done by sterilizing the thin film evaporator, steaming-in-place or other techniques known in the art, and by feeding and extracting the suspension under aseptic conditions. In addition, both the aqueous and ethanolic solutions can be sterile filtered before or during the injection process.

The examples presented below are provided as a further guide to the practitioner of ordinary skill in the art, and are not to be construed as limiting the invention in any way.

EXAMPLE 1

Preparation of KL4 Pulmonary Surfactant Liposome Composition 1L of 40 mg/ml total phospholipid KL4 pulmonary surfactant is prepared by ethanol injection. 22.5 g DPPC, 7.5 g POPG, 4.5 g palmitic acid and 0.8 g KL4 peptide are dissolved in 250 ml 95% ethanol and sterile filtered into sterile tris buffer at 45° C.

Removal of residual ethanol is effected by thin-film evaporation using a rotary thin-film evaporator with an internal evaporative surface of 0.25 ft$^2$ and a film thickness of 1/32 inch. Two passes through the thin film evaporator are preferable to achieve an ethanol content below 0.1% w/w in the final product. The material prepared by ethanol injection as described above is first diluted with sterile-filtered Water For Injection and then fed into the thin-film evaporator. As the material passes continuously through the thin film evaporator, ethanol and water are removed. The residence time for the material in the thin-film evaporator is approximately 1 minute. The conditions for each pass through the thin-film evaporator are as follows:

| | |
|---|---|
| Feed rate: | 45 mL/min |
| Product Temperature: | 40° C. |
| Pressure: | 30–80 mm Hg |
| Feed temperature: | 5–20° C. |
| Receiver temperature: | 5–15° C. |
| Pass 1 dilution: | 1.3 L sterile-filtered Water for Injection |
| Pass 2 dilution: | 0.54 L sterile-filtered Water for Injection |

Once the material has passed through the thin-film evaporator, it is cooled to 5–15° C. in the receiving vessel.

EXAMPLE 2

A 15L batch of 40 mg/ml total phospholipid KL4 pulmonary surfactant is prepared in accordance with the procedure of Example 1 using 337.5 g DPPC, 112.5 g POPG, 67.5 g palmitic acid and 12 g KL4 peptide in 3.75L 95% ethanol.

EXAMPLE 3

Viscosity-Temperature Experiments

Three 300 ml batches of KL4 pulmonary surfactant liposome composition were prepared by ethanol injection using thin film evaporation in accordance with the procedure of Example 1.

The product temperature at which the thin film evaporation was conducted was varied for the batches and the viscosity of the resulting product measured. Batches 1 and 3 were prepared below the transition temperature range at about 32° C. while batch 2 was prepared within the transition temperature range, at about 40° C. The viscosity of the material was then measured using a Brookfield DVII Viscometer. The results, are set forth below in Table 1.

TABLE 1

| | VISCOSITY (cPs) | | | | | | | | | |
|---|---|---|---|---|---|---|---|---|---|---|
| RPM | 1 min | 2 min | 3 min | 4 min | 5 min | 6 min | 7 min | 8 min | 9 min | 10 min |
| BATCH 1 | | | | | | | | | | |
| 0.3 | 5000 | 46670 | 44170 | 35000 | 30030 | 30830 | 30000 | 30000 | 30000 | 30000 |
| 1 | 13250 | 13250 | 13250 | 13250 | 13250 | 13000 | 13000 | 13000 | 13000 | 13000 |
| 10 | 4850 | 4300 | 3975 | 3775 | 3600 | 3475 | 3375 | 3300 | 3250 | 3175 |
| BATCH 2 | | | | | | | | | | |
| 0.3 | 4167 | 4167 | 4167 | 4167 | 4167 | 2500 | 2500 | 3333 | 2500 | 2500 |
| 1 | 1000 | 1000 | 1000 | 1000 | 1000 | 1000 | 1250 | 1250 | 1000 | 1000 |
| 10 | 1000 | 1000 | 925.0 | 875.0 | 850.0 | 825.0 | 800.0 | 775.0 | 750.0 | 750.0 |
| BATCH 3 | | | | | | | | | | |
| 0.3 | 35830 | 32500 | 31670 | 29170 | 29170 | 27500 | 26670 | 26670 | 26620 | 24670 |
| 1 | 11000 | 10750 | 11250 | 11250 | 11250 | 11250 | 11250 | 11250 | 11250 | 11000 |
| 10 | 4825 | 4150 | 3800 | 3600 | 3500 | 3450 | 3375 | 3350 | 3325 | 3250 |

The conditions for each pass through the thin film evaporator for the three batches were as follows:

| Batch 1 (Control) | |
|---|---|
| Feed rate: | ~20 ml/min |
| Product temp.: | ~32° C. |
| Pressure: | ~26 mm Hg |
| Batch 2 | |
| Feed rate: | ~30 ml/min |
| Product temp.: | ~40° C. |
| Pressure: | ~38–40 mm Hg |
| Batch 3 | |
| Feed rate: | ~20 ml/min |
| Product Temp.: | ~32° C. |
| Pressure: | ~26 mm Hg |

The foregoing results demonstrate the Batch 2, prepared within the transition temperature range of the surfactant composition, exhibited greatly reduced viscosity compared to batches 1 and 3 prepared at a lower product temperature.

What is claimed is:

1. In a process for preparing a liposomal suspension of $KL_4$ peptide by alcoholic ethanolic injection, wherein a solution of the peptide and an encapsulating amount of a suitable lipid in an alcoholic solvent is prepared and injected into an aqueous solution; the improvement which comprises removing the alcoholic solvent by thin-film evaporation within the transition temperature range of the liposomal suspension.

2. The process of claim 1 wherein the alcoholic solvent is ethanol.

3. The process of claim 1 wherein the suitable lipid is selected from the group consisting of dipalmitoyl-phosphatidylcholine (DPPC), palmitoyloleoylphosphatidylglycerol (POPG), palmitic acid (PA), egg phosphatidylcholine (EPC), egg phosphatidylglycerol (EPG), cholesterol, dimyristoylphosphatidylglycerol (DMPG) and dimyristoylphosphatidylcholine (DMPC).

4. The process of claim 1 wherein the liposomal suspension is KL4 pulmonary surfactant.

5. The process of claim 4 wherein the transition temperature range is approximately 35–50° C.

6. The process of claim 1 wherein the alcoholic solvent is a lower alkanol of one to six carbon atoms.

7. The process of claim 1 wherein the alcoholic solvent contains a peptide solubilizing amount of a fluorinated alcohol.

8. The process of claim 1 wherein the alcoholic solvent contains a peptide solubilizing amount of a aprotic solvent.

* * * * *

UNITED STATES PATENT AND TRADEMARK OFFICE
CERTIFICATE OF CORRECTION

PATENT NO. : 6,120,795
DATED : September 19, 2000
INVENTOR(S) : Robert Klimchak and Peter Glavinos It is certified that error appears in the above-identified patent and that said Letters Patent is hereby corrected as shown below:

Claim 1 - Column 7, line 25, after the word "alcoholic" please delete "ethanolic"

Signed and Sealed this

Fifteenth Day of May, 2001

Attest:

NICHOLAS P. GODICI

Attesting Officer     Acting Director of the United States Patent and Trademark Office